United States Patent
Chen

(10) Patent No.: US 9,125,599 B2
(45) Date of Patent: Sep. 8, 2015

(54) SYSTEMS AND METHODS FOR BALANCING INFRARED ILLUMINATION IN EYE IMAGING

(71) Applicant: AMO Development LLC., Santa Ana, CA (US)

(72) Inventor: Li Chen, San Jose, CA (US)

(73) Assignee: AMO DEVELOPMENT, LLC, Santa Ana, CA (US)

( * ) Notice: Subject to any disclaimer, the term of this patent is extended or adjusted under 35 U.S.C. 154(b) by 0 days.

(21) Appl. No.: 14/102,210

(22) Filed: Dec. 10, 2013

(65) Prior Publication Data

US 2014/0176906 A1 Jun. 26, 2014

Related U.S. Application Data

(60) Provisional application No. 61/745,080, filed on Dec. 21, 2012.

(51) Int. Cl.
*A61B 3/14* (2006.01)
*A61B 3/00* (2006.01)

(52) U.S. Cl.
CPC ........................................ *A61B 3/14* (2013.01)

(58) Field of Classification Search
USPC .................................................. 351/200–246
See application file for complete search history.

(56) References Cited

U.S. PATENT DOCUMENTS

| | | | | |
|---|---|---|---|---|
| 5,106,184 A * | 4/1992 | Milbocker | .................... | 351/221 |
| 6,916,096 B2 * | 7/2005 | Eberl et al. | .................... | 351/209 |
| 7,976,162 B2 * | 7/2011 | Flitcroft | ........................ | 351/209 |
| 8,764,188 B2 * | 7/2014 | Tabor | ............................ | 351/201 |

\* cited by examiner

*Primary Examiner* — Mohammed Hasan

(57) ABSTRACT

The field of the invention relates to systems and methods for eye imaging and, more particularly, for balancing illuminations in eye imaging. An asymmetric illumination method to compensate for the imbalance illumination caused by nose reflection is described. In one embodiment, a method for balancing illuminations in eye imaging comprises generating one or more eye images, using the images to detect the imbalance illuminations from the nasal sclera and temporal sclera with the selected region of interest. In another embodiment, a system for balancing illuminations in eye imaging uses the detected imbalance illumination ratio of nasal/temporal sclera as the signal for adjusting the brightness of the infrared LEDs for asymmetric illumination.

7 Claims, 10 Drawing Sheets

| | Eye | Imbalance Ratio (%) |
|---|---|---|
| Patient1 | OD | 40.72 |
| | OS | 24.55 |
| Patient2 | OD | 26.91 |
| | OS | 30.63 |

Fig. 4e

SYSTEMS AND METHODS FOR BALANCING INFRARED ILLUMINATION IN EYE IMAGING

CROSS REFERENCE TO RELATED APPLICATIONS

This application claims the benefit of priority to U.S. Provisional Patent Application Ser. No. 61/745,080 filed on Dec. 21, 2012, the entire disclosure of which is incorporated herein by reference.

FIELD OF THE INVENTION

The present invention relates to eye imaging and, more particularly, to balancing infrared illuminations in eye imaging.

BACKGROUND OF THE INVENTION

Current ophthalmic diagnostic and measurement systems typically use wavefront acquisition and diagnostic capabilities to deliver measurement accuracy, thereby enhancing the precision of laser vision correction surgery. An exemplary ophthalmic diagnostic and measurement product using wavefront is the Abbott WaveScan WaveFront System, which, among having other capabilities and technologies, uses a Shack-Hartmann wavefront sensor that can quantify aberrations throughout the entire optical system of the patient's eye, including second-order aberrations related to spherical error and cylindrical errors, and higher-order aberrations related to coma, trefoil, and spherical aberrations. An exemplary wavefront diagnostic system was described in U.S. Pat. No. 7,931,371 to Dai, and is herein incorporated by reference in its entirety.

In addition to its use in ophthalmic diagnostic and measurement systems, laser technology has become the technique of choice for ophthalmic surgical applications, such as refractive surgery for correcting myopia, hyperopia, astigmatism, and so on, as well as procedures for treating and removing a cataractous lens. Known laser-assisted ophthalmic surgical systems typically use a variety of forms of lasers and/or laser energy to effect vision correction, including infrared lasers, ultraviolet lasers, picosecond lasers, femtosecond lasers, wavelength multiplied solid-state lasers, and the like. Laser-assisted ophthalmic surgical systems often also use wavefront diagnostic systems to accurately measure the refractive characteristics of a particular patient's eye.

A wavefront diagnostic system generally captures eye images during wavefront measurement. A pupil camera in an aberrometer captures images of the eye, illuminated by infrared light-emitting diodes (LEDs) designed as a symmetric configuration. These eye images are used, for example, for iris registration for laser vision correction. Eye images from the diagnostic system, however, often show the sclera on the nasal side as appearing brighter than the sclera on the temporal side. This is true for both the right eye and the left eye. The eye image is essential for wavefront-guided corneal refractive surgery since it identifies the treatment area and is used for eye tracking. The pupil itself is not a reliable marker for the treatment area because its size and center change depending on the lighting condition or administered medication. The outer iris boundary (OIB), a circular boundary between the iris and the sclera of the eye, however, is fixed. The aberrometer thus identifies this boundary from the eye image for the iris registration for laser vision correction. But, most eye images captured by the pupil camera show that the sclera on the nasal side looks brighter than the sclera on the temporal side, both from the right eye (OD) and the left eye (OS). This imbalance illumination is typically caused by secondary reflections of infrared LEDs by the patient's nose. FIG. 1 shows typical eye images, captured during wavefront measurement where the pupil illumination uses infrared LEDs. The image shows the sclera on the nasal side appearing brighter than the sclera on the temporal side for both the right eye (OD) and the left eye (OS). The imbalance illumination can cause failure in detecting the OIB, and as such, it is desirable to correct it in the diagnostic system for laser-assisted ophthalmic surgery.

Accordingly, improved systems and methods for balancing infrared illuminations in eye imaging are desirable.

SUMMARY OF THE INVENTION

The field of the invention generally relates to systems and methods for eye imaging and, more particularly, for correcting the imbalance illumination caused by nose reflections in eye imaging. Use of an asymmetric illumination method to compensate for the imbalance illumination caused by the nose reflection is described. In one embodiment, a method for balancing infrared illumination in eye imaging comprises generating one or more eye images, using the images to detect the imbalance illuminations from the nasal sclera and temporal sclera with the selected region of interest ("ROI"). In another embodiment, a system for balancing illuminations in eye imaging uses the detected imbalance illumination ratio of nasal/temporal sclera as the signal for adjusting the brightness of the infrared LEDs for asymmetric illumination.

Other systems, methods, features and advantages of the invention will be or will become apparent to one with skill in the art upon examination of the following drawings and detailed description. It is intended that all such additional systems, methods, features and advantages be included within this description, be within the scope of the invention, and be protected by the accompanying claims.

BRIEF DESCRIPTION OF THE DRAWINGS

To better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than depicted literally or precisely.

FIG. 4e shows imbalance illumination ratios of two patients according to a preferred embodiment of the present invention.

DETAILED DESCRIPTION OF THE PREFERRED EMBODIMENTS

The present invention is generally directed to systems and methods for balancing infrared illuminations in eye imaging. An embodiment of the invention generally balances the infrared illuminations in eye imaging by extracting the nasal and temporal imbalance illumination ratio in the eye images, and using the imbalance ratio to adjust the infrared LED's brightness for nasal and temporal illumination, thereby compensating for the imbalance.

The balancing of infrared illumination as described in the preferred embodiments of the invention may be used in stand-alone ophthalmic diagnostic and measurement systems, in a laser eye surgery system having an integrated ophthalmic diagnostic and measurement system, in an eye tracking system of an ophthalmic surgical system, and the like.

Figure 1:
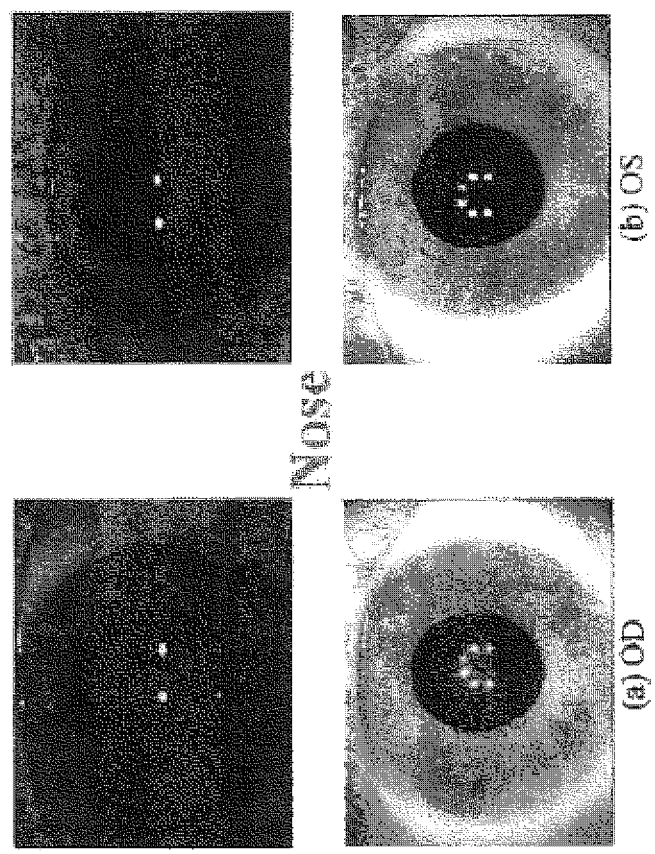
FIG. 1 shows exemplary eye images.
Figure 2A:
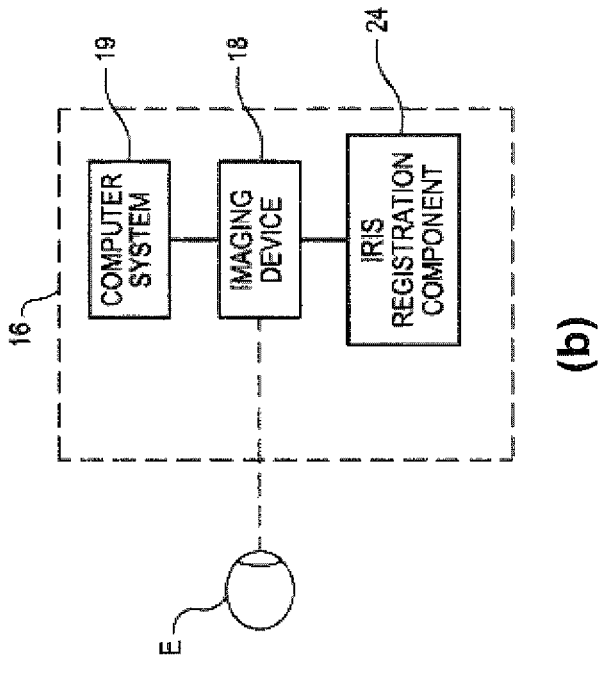
FIG. 2a schematically illustrates simplified measurement systems according to a preferred embodiment of the present invention.
Figure 2A:
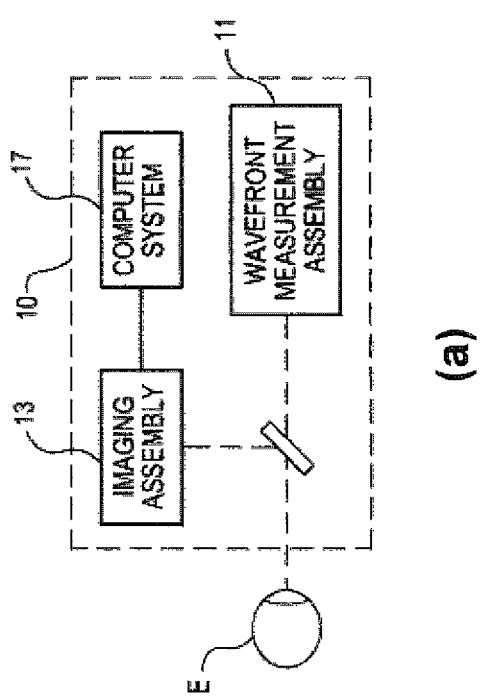
Figure 2A:
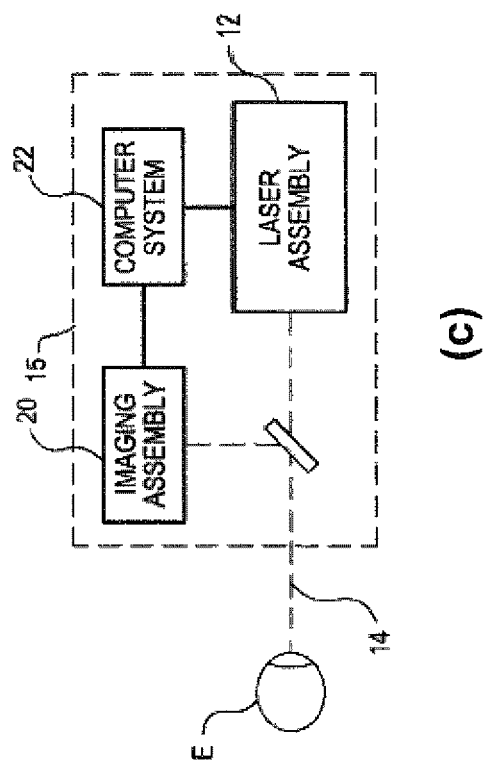

Turning to FIG. 2a, illustrations of a first measurement system 10 and a second measurement system 16 are shown. In an embodiment, the first measurement system 10 is a wavefront measurement device 10 that measures aberrations and other optical characteristics of an ocular or other optical tissue system. The data from such a wavefront measurement device may be analyzed by a computer system 17 and used to generate an optical surface from an array of optical gradients.

In another embodiment, the second measurement system 16 is a corneal topographer 16. Corneal topographer 16 may be used to diagnose and examine the corneal surface. Corneal topographer 16 typically includes an imaging device 18, such as a frame grabber that takes images of the cornea. The images obtained by the frame grabber are analyzed by a computer system 19, and the computer system 19 may generate one or more graphical and/or tabular outputs, including three dimensional topographical maps.

Figure 2B:
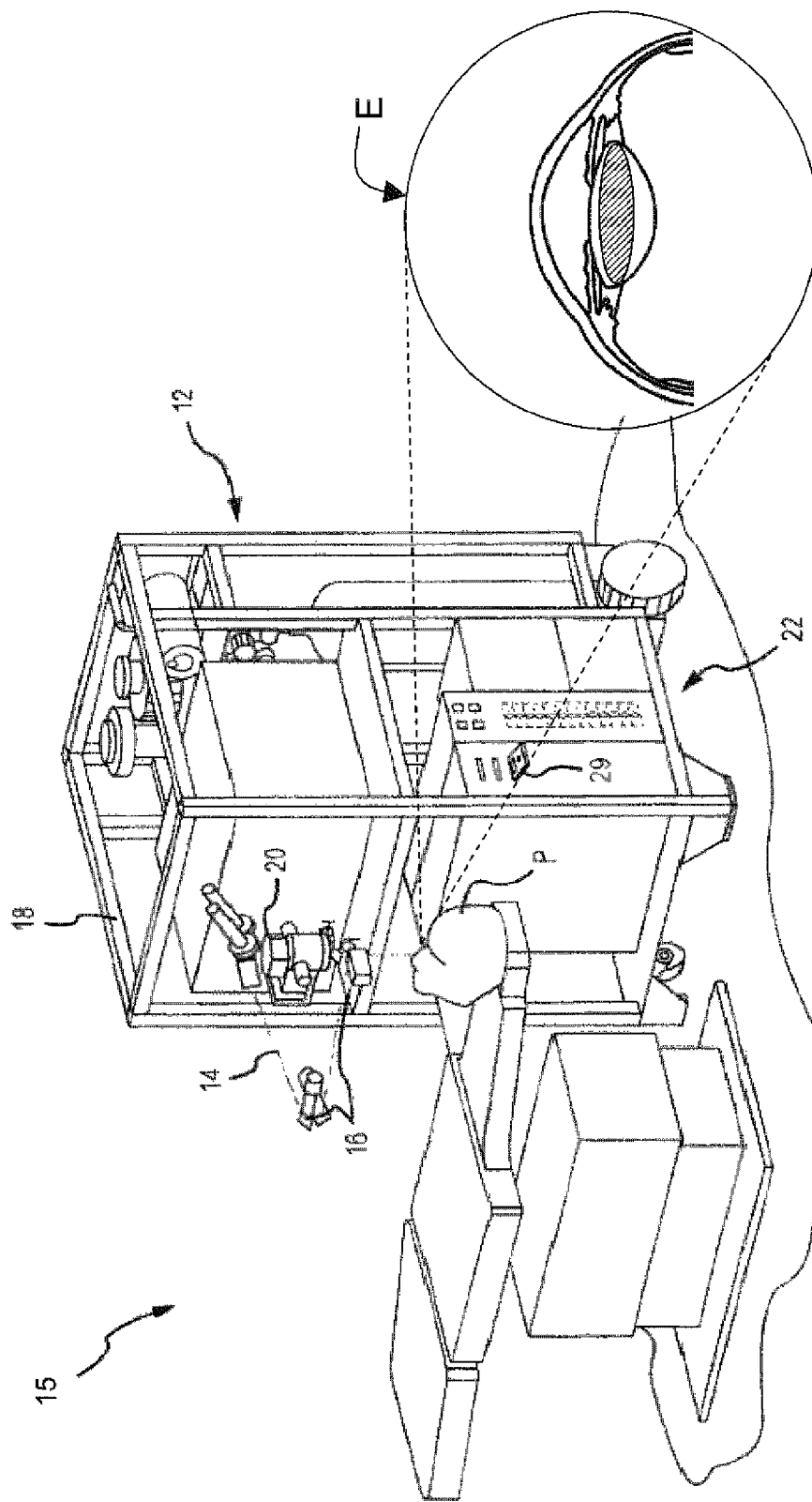
FIG. 2b is a perspective view of a laser eye surgery system according to a preferred embodiment of the present invention.

Turning to FIG. 2b, illustration of a laser surgery system 15 is shown. In an embodiment, the laser surgery system 15 includes a laser assembly 12 that produces a laser beam 14. Laser assembly 12 is optically coupled to laser delivery optics 16, which directs laser beam 14 to an eye E of a patient. An imaging assembly 20, including a microscope, is mounted on a delivery optics support structure (not shown here, but for clarity, see incorporated U.S. Pat. No. 7,931,371 and other herein incorporated patents for further detail) to image the cornea of eye E during the laser procedure. Laser assembly 12 generally comprises an excimer laser source, typically comprising an argon-fluorine laser producing pulses of laser light having a wavelength of approximately 193 nm. Laser assembly 12 may be designed to provide a feedback stabilized fluence at the patient's eye E, delivered via delivery optics 16. Although an excimer laser is the illustrative source of an ablating beam, other lasers may be used.

Laser assembly 12 and delivery optics 16 generally direct laser beam 14 to the eye E under the direction of a computer system 22. Computer system 22 may selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system will be under computer control of computer system 22 to affect the desired laser sculpting process so as to deliver a customized ablation profile, with the computer system 22 ideally altering the ablation procedure in response to inputs from an optical feedback system (not shown here, but for clarity, see incorporated U.S. Pat. No. 7,931,371 and other herein incorporated patents for further detail). The feedback may be input into computer system 22 from an automated image analysis system 21, or may be manually input into the processor by a system operator using a user input interface device 62 (FIG. 3) in response to a visual inspection of analysis images provided by the optical feedback system. Computer system 22 often continues and/or terminates a sculpting treatment in response to the feedback, and may optionally also modify the planned sculpting based at least in part on the feedback.

Computer system 17, 19, 22 may comprise (or interface with) a conventional or special computer, such as a personal computer (PC), laptop, and so on, including the standard user interface devices such as a keyboard, a mouse, a touch pad, foot pedals, a joystick, a touch screen, an audio input, a display monitor, and the like. Computer system 17, 19, 22 typically includes an input device such as a magnetic or optical disk drive, or an input interface such as a USB connection, a wired and/or wireless network connection, or the like. Such input devices or interfaces are often used to download a computer executable code, to a storage media 29, embodying any of the methods of the present invention. Storage media 29 may take the form of an optical disk, a data tape, a volatile or non-volatile memory, RAM, or the like, and the computer system 17, 19, 22 includes the memory and other standard components of modern computer systems for storing and executing this code. Storage media 29 may alternatively be remotely operatively coupled with computer system 22 via network connections such as LAN, the Internet, or via wireless methods such as WLAN, Bluetooth, or the like.

Additional components and subsystems may be included with laser system 15, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference.

Figure 3:
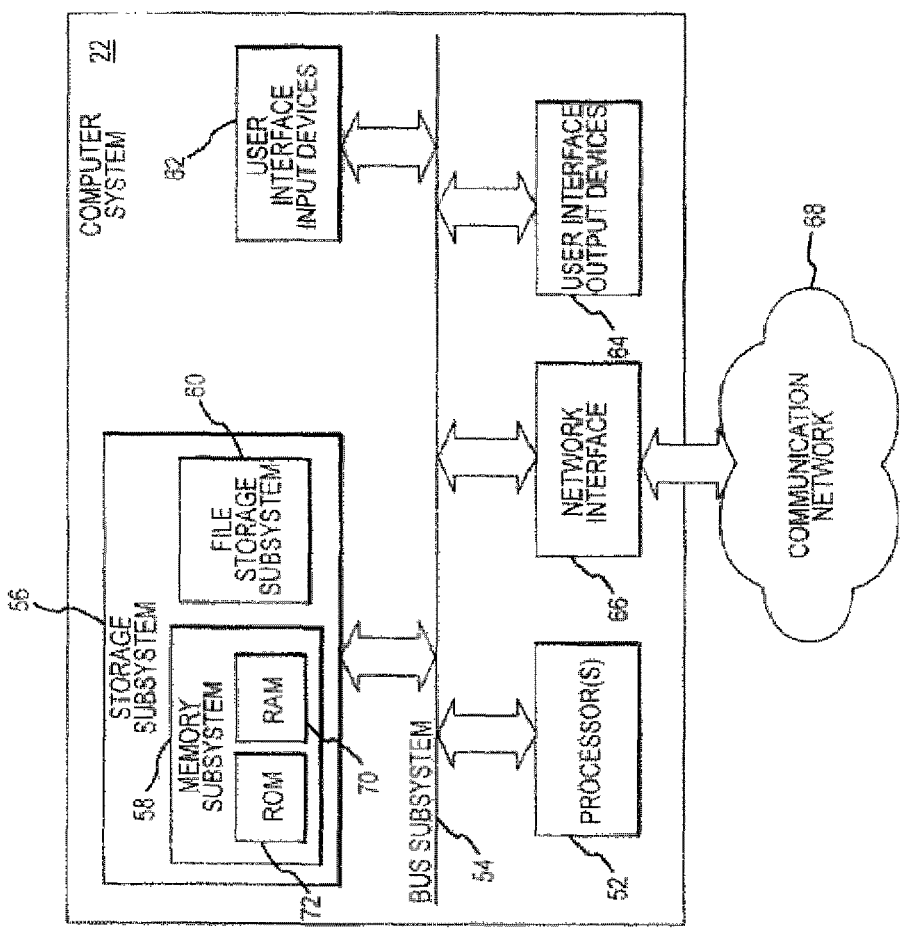
FIG. 3 is a simplified diagram of a computer system according to a preferred embodiment of the present invention.

FIG. 3 is a simplified block diagram of an exemplary computer system 17, 19, 22 that may be used in measurement instrument 10, measurement instrument 16, and laser surgical system 15. Computer system 17, 19, 22 typically includes at least one processor 52 which may communicate with a number of peripheral devices via a bus subsystem 54. These peripheral devices may include a storage subsystem 56, comprising a memory subsystem 58 and a file storage subsystem 60 (which may include storage media 29), user interface input devices 62, user interface output devices 64, and a network interface subsystem 66. Network interface subsystem 66 provides an interface to outside networks 68 and/or other devices.

User interface input devices 62 may include a keyboard, pointing devices such as a mouse, trackball, touch pad, or graphics tablet, a scanner, foot pedals, a joystick, a touch screen incorporated into the display, audio input devices such as voice recognition systems, microphones, and other types of input devices. User interface input devices 62 are often used to download a computer executable code from a storage media 29 embodying any of the methods of the present invention. User interface input devices 62 are also used to control an eye fixation system. In general, use of the term "input device" is intended to include a variety of conventional and proprietary devices and ways to input information into computer system 17, 19, 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 17, 19, 22 to a system operator.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include storage media 29 (FIG. 2b). File storage subsystem 60 may include a hard disk drive along with associated removable media, a Compact Disk (CD) drive, an optical drive, DVD, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 17, 19, 22 communicate with each other as intended. The various subsystems and components of computer system 17, 19, 22 need not be at the same physical location but may be distributed at various locations within a distributed network. Although bus subsystem 54 is shown schematically as a single bus, alternate embodiments of the bus subsystem may use multiple busses.

Computer system 17, 19, 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 17, 19, 22 depicted in FIG. 3 is intended only as an example for purposes of illustrating one embodiment of the present invention. Many other configurations of computer system 22, having more or fewer components than the computer system depicted in FIG. 3, are possible.

Figure 4A:
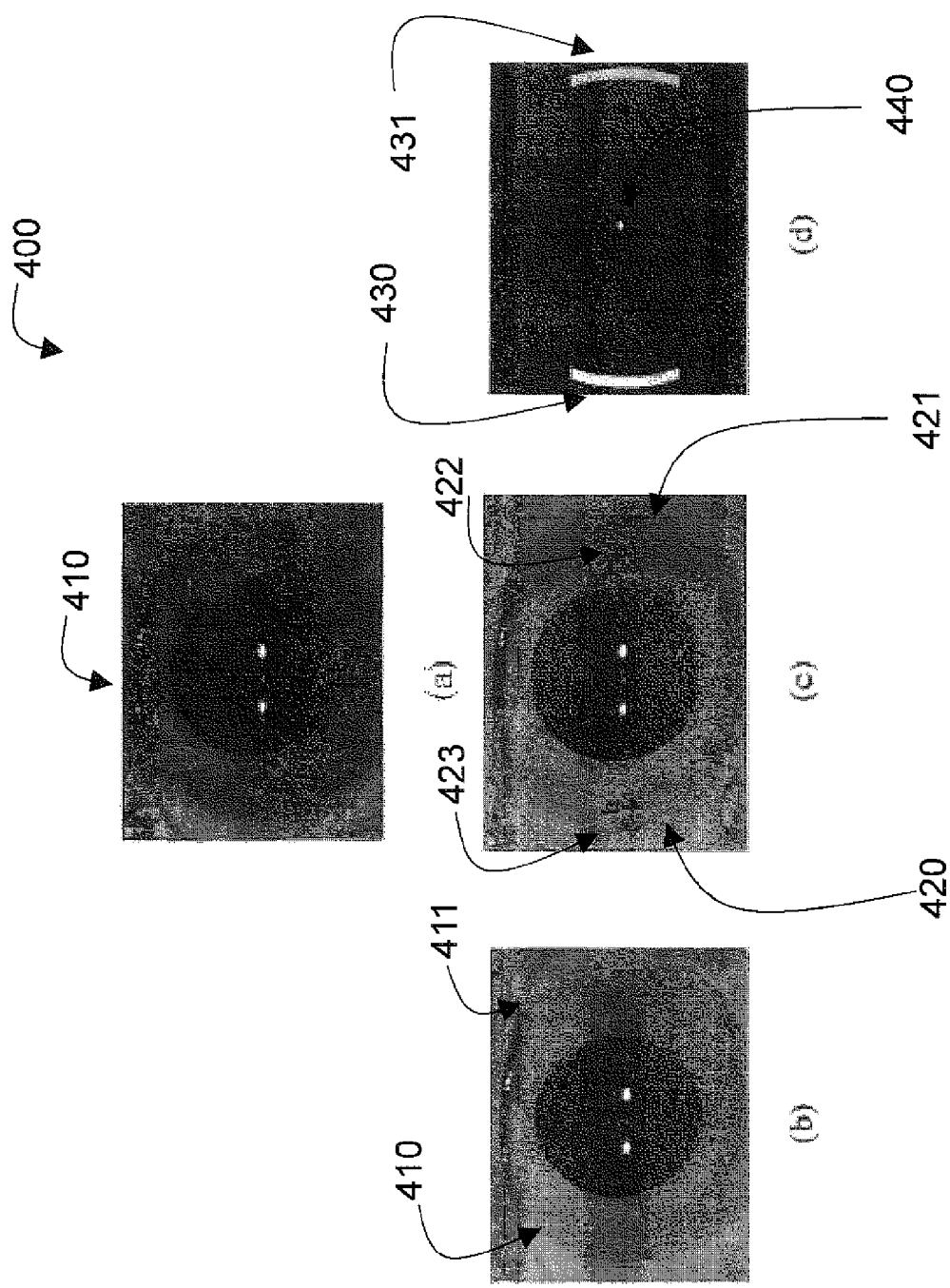
FIG. 4a shows eye images according to a preferred embodiment of the present invention.

Turning to FIG. 4a, an exemplary technique for detection of imbalance illumination 400 is illustrated. Eye images captured by the pupil camera of measurement system 10, 16 or laser surgery system 15 are analyzed to estimate the imbalance illumination level at the sclera on the nasal and the temporal sides. FIG. 4a shows the raw eye image 410 in image (a) and the detected outer iris boundary (OIB) 410, 411 in image (b) using image processing of the image analysis system 21. From the detected OIB 410, 411 information, two regions of interest (ROI) 420, 421 may be selected on the sclera in the eye image, including one on the nasal side 420 and one on the temporal side 421, shown in image (c). The ROIs may be automatically selected, or manually selected by a system operator. The ROIs 420, 421 are typically located just outside of the OIB. Parameter a 422 and b 423 may then be generated automatically or by the system operator. Parameter a represents the desired height of ROIs 420, 421. Parameter b 423 represents the desired width of ROIs 420, 421. Image (d) shows an exemplary extracted eye image of ROIs 430, 431, after applying parameters a and b, and which will be used to calculate the imbalance illumination ratio of the nasal and temporal sides on the sclera. The dot 440 in image (d) is the center of OIB.

Figure 4B:
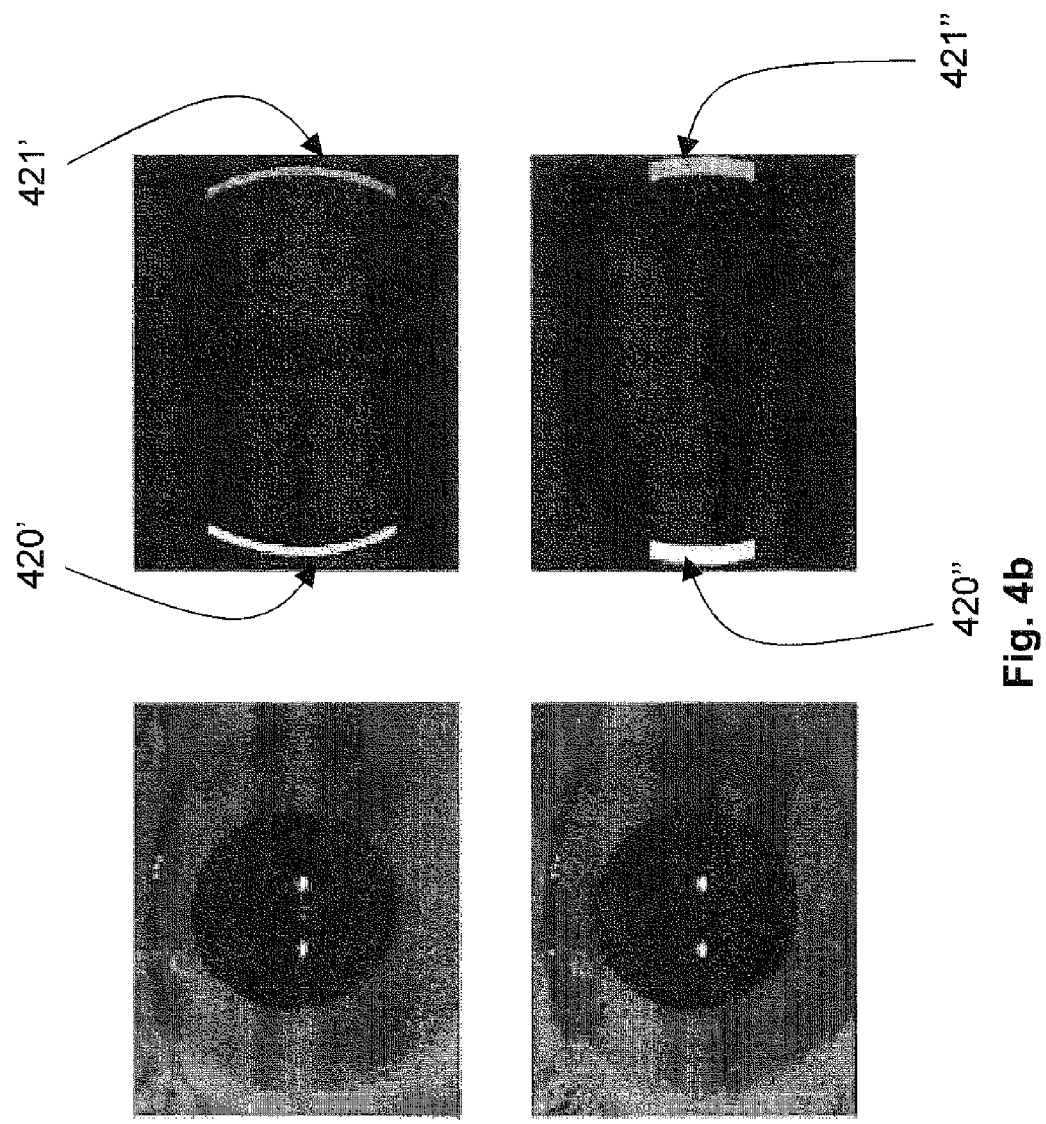
FIG. 4b shows other eye images according to a preferred embodiment of the present invention.

Turning to FIG. 4b, to avoid the patient's eyelid getting into the selected ROI, parameter a 422 and parameter b 423 may be used to change the size and location of ROIs 420, 421, as shown in ROIs 420', 421', and 420", 421."

After the desired ROIs have been selected, average intensity of the ROIs can be calculated as following, $$I_{nasal} = \text{mean}(I_{ROI_n})$$
$$I_{temporal} = \text{mean}(I_{ROI_t})$$

$I_{nasal}$ is the average intensity of the ROIs on the nasal side, while $I_{temporal}$ is the average intensity of the ROIs on the temporal side.

Then the imbalance illumination ratio of the nasal and temporal sides of the sclera can be calculated as following, $$\text{Ratio} = \frac{|I_{nasal} - I_{temporal}|}{\text{mean}(I_{nasal}, I_{temporal})}$$

This imbalance ratio can be used to adjust, (either automatically or manually by the system operator), the infrared LED's brightness for nasal and temporal illumination to compensate for the imbalance illumination caused by nasal reflection in the eye image. The adjustment and compensation may be repeated until the imbalance ratio reaches a predetermined or desired tolerance level, e.g., 10%.

Figure 4C:
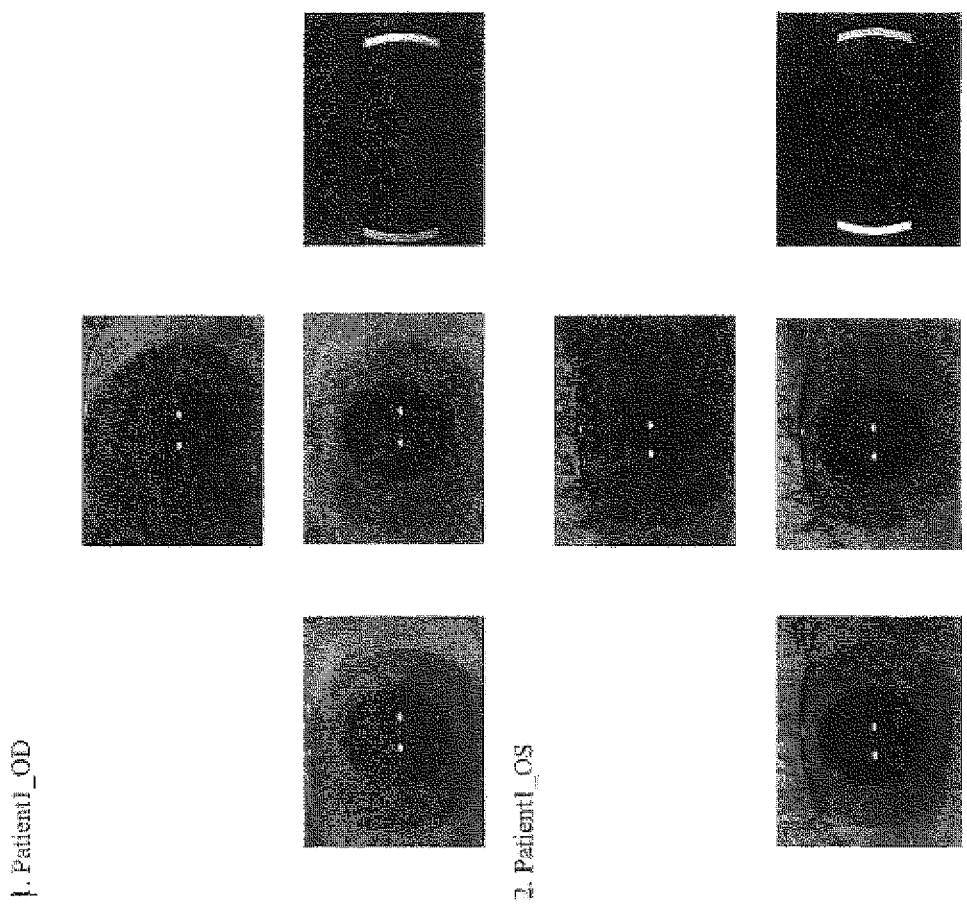
FIG. 4c shows eye images of a patient according to a preferred embodiment of the present invention.
Figure 4D:
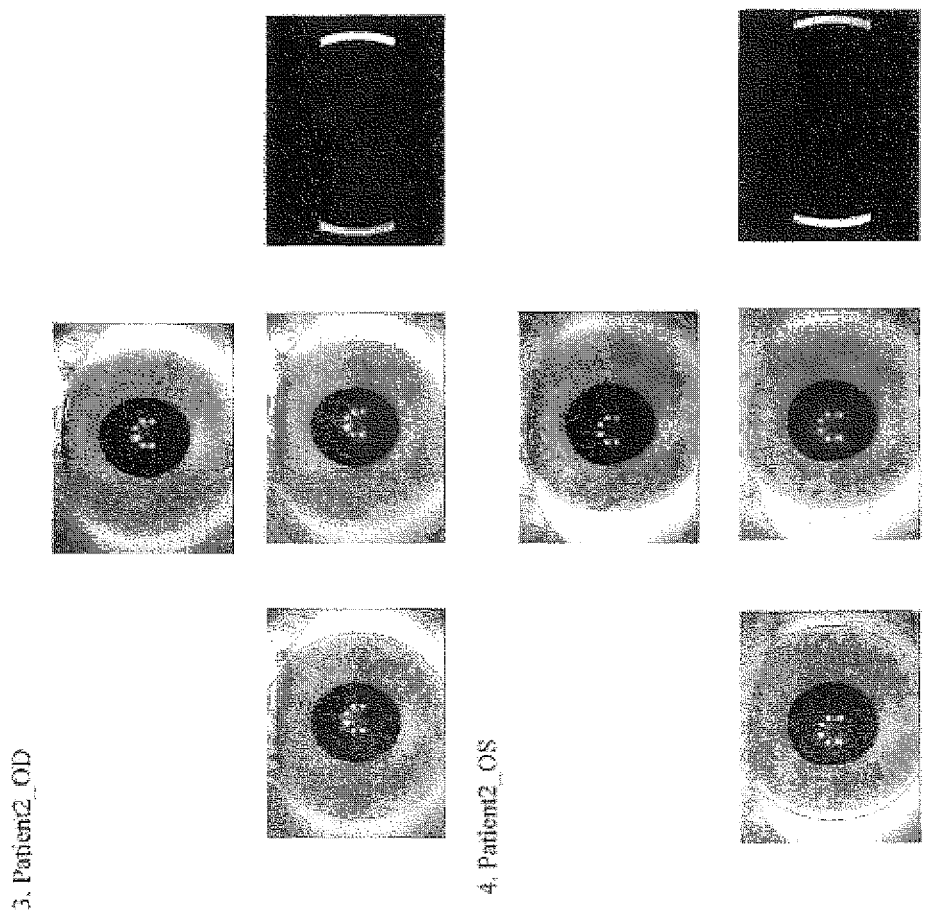
FIG. 4d shows eye images of another patient according to a preferred embodiment of the present invention.

Turning to FIGS. 4c-4e, in another embodiment, the exemplary imbalance illumination ratios of two patients are shown. FIG. 4c shows eye images captured by one diagnostic system from patient1 and patient2 with selected ROIs. FIG. 4d shows eye images captured by another diagnostic system from patient3 and patient4 with selected ROIs. FIG. 4d shows a table of imbalance ratio detected from the four eyes.

Figure 5:
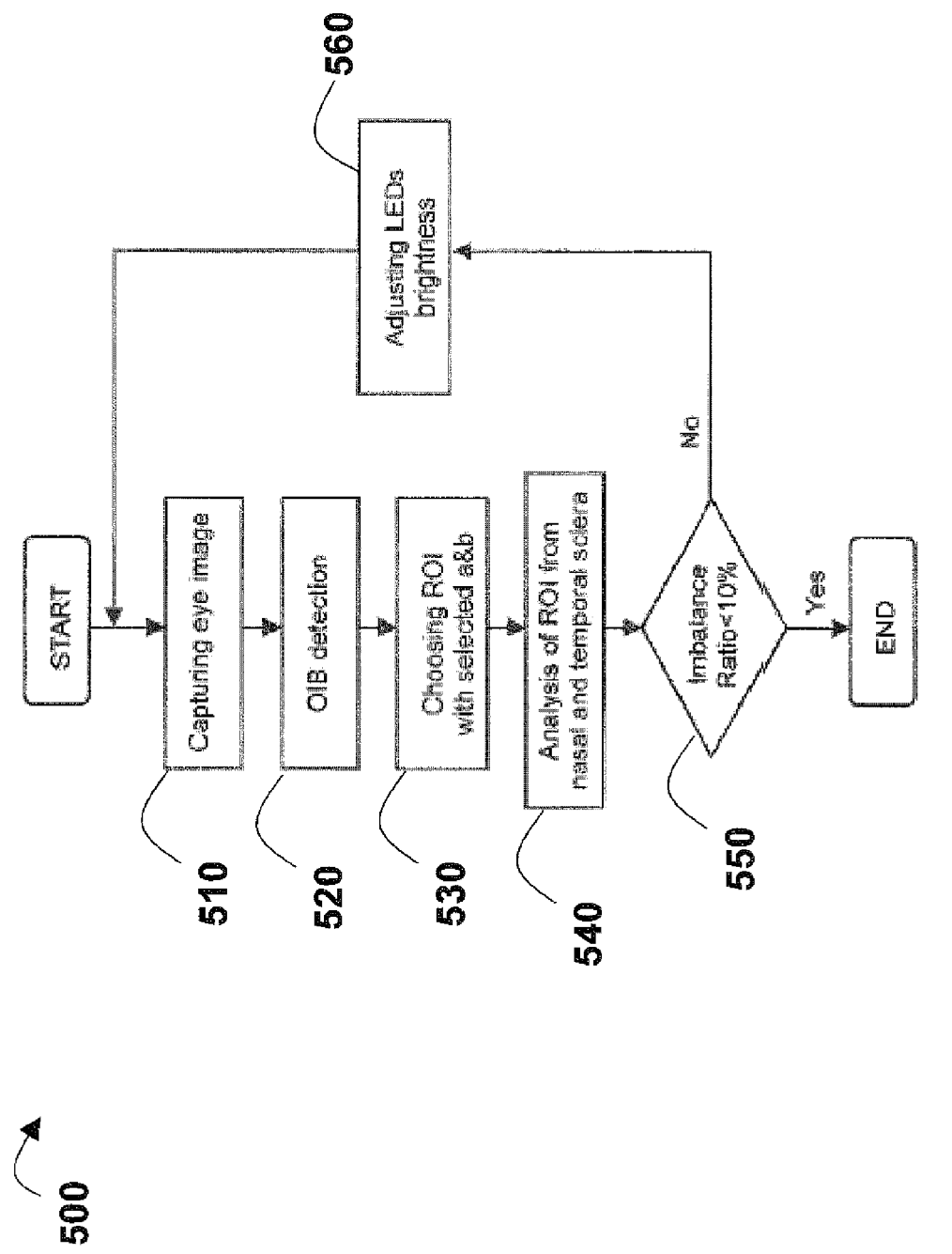
FIG. 5 is a flowchart illustrating a process according to a preferred embodiment of the present invention.

Turning to FIG. 5, a process 500 for imbalance illumination detection and compensation according to an embodiment of the invention is shown. The process starts with a first set of (raw) eye images taken by the diagnostic and measurement system (Action Block 510). The OIB is detected from the eye images using image processing (Action Block 520). From the detected OIB information, parameters a and b are generated and ROIs are selected with the generated parameters a and b (Action Block 530). The ROIs from the nasal and temporal sclera are analyzed using their average intensities, which are in turn used to calculate the imbalance ratio (Action Block 540). If the imbalance ratio does not reach a predetermined or desired tolerance level (Decision Block 550), e.g., <10%, then the brightness of the LEDs may be adjusted (Action Block 560) until the desired tolerance level is reached.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein are merely illustrative and that the invention may appropriately be performed using different or additional process actions or a different combination or ordering of process actions. For example, while this invention is particularly suited for wavefront acquisition and diagnostic system, and/or laser-based ophthalmic surgical systems, it can be used for any acquisition and diagnostic system and/or ophthalmic surgical system.

Additionally and obviously, features may be added or subtracted as desired. Accordingly, the invention is not to be restricted except in light of the attached claims and their equivalents.

What is claimed is:

1. An eye imaging assembly comprising:
   an imaging device positioned to capture an image of a patient's eye;
   an illumination device positioned to illuminate the patient's eye;
   a processor operatively coupled to the imaging device; and
   a computer readable medium that stores a computer program that, when executed, causes the processor to perform or enable the following steps:
   capturing an eye image of the patient's eye with the imaging device;
   detecting an outer iris boundary within the captured eye image;
   selecting a first region of interest in a nasal sclera area and a second region of interest in a temporal sclera area within the captured eye image;
   calculating a ratio of illumination imbalance between illumination of the first region of interest and illumination of the second region of interest within the captured eye image;
   adjusting the illumination device; and
   repeating the adjusting, capturing, detecting, selecting, and calculating steps until the ratio of illumination imbalance reaches a predetermined tolerance level.

2. The eye imaging assembly of claim 1, wherein the selection of the first region of interest and the second region of interest is based on a desired width and a desired height limited by a field of view and eyelids.

3. The eye imaging assembly of claim 1, wherein the predetermined tolerance level is about 10 percent.

4. The eye imaging assembly of claim 1, wherein the illumination device is an infrared illumination device.

5. The eye imaging assembly of claim 1, wherein the illumination device is an asymmetric illumination device with adjustable brightness for nasal and temporal illumination of the patient's eye, and wherein the adjusting step includes adjusting brightness of the illumination device for nasal and temporal illumination.

6. The eye imaging assembly of claim 1, wherein the ratio of illumination imbalance is calculated from an average intensity of the first region of interest within the eye image and an average intensity of the second region of interest within the eye image.

7. The eye imaging assembly of claim 6, wherein the ratio of illumination imbalance is defined as a ratio of a difference between the average intensity of the first region of interest and the average intensity of the second region of interest to a mean of the average intensity of the first region of interest and the average intensity of the second region of interest.

* * * * *